(12) United States Patent
Schwartz et al.

(10) Patent No.: US 12,734,053 B2
(45) Date of Patent: Sep. 15, 2026

(54) ABSORBABLE INTRAVASCULAR STENTS HAVING A THERAPEUTIC DRUG WITHIN THE SCAFFOLD

(71) Applicant: EFEMORAL MEDICAL, INC., Los Altos, CA (US)

(72) Inventors: Lewis B. Schwartz, Lake Forest, IL (US); Ivan Tzvetanov, Mountain View, CA (US); Alex Estrada, Menlo Park, CA (US); Eugene Michal, San Anselmo, CA (US)

(73) Assignee: EFEMORAL MEDICAL, INC.

( * ) Notice: Subject to any disclaimer, the term of this patent is extended or adjusted under 35 U.S.C. 154(b) by 289 days.

(21) Appl. No.: 18/578,101

(22) PCT Filed: Aug. 10, 2022

(86) PCT No.: PCT/US2022/040014

§ 371 (c)(1),
(2) Date: Jan. 10, 2024

(87) PCT Pub. No.: WO2023/018844

PCT Pub. Date: Feb. 16, 2023

(65) Prior Publication Data

US 2024/0315857 A1 Sep. 26, 2024

Related U.S. Application Data

(60) Provisional application No. 63/231,862, filed on Aug. 11, 2021.

(51) Int. Cl.
*A61L 31/06* (2006.01)
*A61F 2/90* (2013.01)
(Continued)

(52) U.S. Cl.
CPC ................ *A61F 2/90* (2013.01); *A61L 31/06* (2013.01); *A61L 31/10* (2013.01); *A61L 31/148* (2013.01);
(Continued)

(58) Field of Classification Search
CPC ......... A61L 2300/606; A61L 2300/608; A61L 31/16; A61L 31/10; A61F 2/91
See application file for complete search history.

(56) References Cited

U.S. PATENT DOCUMENTS 10,232,082 B2 3/2019 You et al.
2004/0230298 A1* 11/2004 Udipi ........................ A61F 2/91 623/1.42
(Continued)

FOREIGN PATENT DOCUMENTS

CN 108771573 B 10/2020
JP 2016-508486 A 3/2016
WO 2014117075 A1 7/2014

OTHER PUBLICATIONS

International Search Report and Written Opinion of the International Searching Authority in relation to International Application No. PCT/US22/40014, dated Feb. 16, 2023, 10 pages.

*Primary Examiner* — Kevin T Truong
(74) *Attorney, Agent, or Firm* — Convergence Intellectual Property Law P.C.; Jonathan Garfinkel

(57) ABSTRACT

Devices, systems, and methods are provided to maintain or enhance blood flow through the blood vessel as a stent. The balloon-expandable, bioresorbable, vascular stent elements are configured to be implanted in the blood vessel are described herein. The stent element comprises a scaffold and coating layer comprising a bioresorbable structural polymer. A therapeutic drug is provided both on a scaffold coating and integrated within the structural polymer of the scaffold. The
(Continued)

method of making the bioresorbable, vascular stent includes an additive manufacturing process described herein.

6 Claims, 8 Drawing Sheets

(51) Int. Cl.
*A61L 31/10* (2006.01)
*A61L 31/14* (2006.01)
*A61L 31/16* (2006.01)

(52) U.S. Cl.
CPC ....... *A61L 31/16* (2013.01); *A61F 2210/0004* (2013.01); *A61F 2210/0076* (2013.01); *A61F 2240/001* (2013.01); *A61F 2250/0067* (2013.01); *A61L 2420/02* (2013.01); *A61L 2420/06* (2013.01)

(56) References Cited

U.S. PATENT DOCUMENTS

2005/0070996 A1* 3/2005 Dinh .................... A61L 31/022 623/1.42
2011/0295279 A1* 12/2011 Stone ................ A61B 17/0482 606/145
2020/0390569 A1 12/2020 Schwartz

* cited by examiner 200
201
202
203

201
202
204
205
206
207
204

ABSORBABLE INTRAVASCULAR STENTS HAVING A THERAPEUTIC DRUG WITHIN THE SCAFFOLD

This application is a 35 U.S.C. § 371 national stage filing of PCT Patent Application Number PCT/US22/40014, filed Aug. 10, 2022, which claims the benefit and priority of U.S. Provisional Patent Application No. 63/231,862, entitled "ABSORBABLE INTRAVASCULAR STENTS HAVING A THERAPEUTIC DRUG WITHIN THE SCAFFOLD", filed on Aug. 11, 2021, the full disclosures of the above referenced applications are incorporated herein by reference.

FIELD OF THE INVENTION

The present application pertains generally to the field of medical devices. More specifically, the present application pertains to the design and manufacture of intravascular stents intended to maintain patency (blood flow) of blood vessels (arteries and veins).

BACKGROUND

Atherosclerotic cardiovascular disease or "hardening of the arteries" is the leading cause of death and disability in the world accounting for nearly one-third of all human mortality. Although some developed nations have made significant strides in modifying risk factors and changing lifestyle behaviors, the global prevalence of atherosclerotic disease is still rising with some projections predicting >23 million annual deaths by the year 2030. The economic burden is staggering; in the United States alone, the estimated yearly cost treating atherosclerosis and its sequelae exceeds $200 billion.

Atherosclerosis is a process of pathological arterial aging. In youth, supple elastin fibers within the arterial media provide the structural elasticity and compliance required for arterial pulsation and pulse wave transmission. Over decades, however, the persistent pressure and motion slowly denatures structural matrix proteins causing elastin fatigue and fracture. The result is a slow but inexorable loss of distensibility; the arterial wall chronically stiffens. With the loss of pulsatility and wave reflection, the flow velocity profile becomes blunted; flow reversal is lost and the modulus of antegrade flow is attenuated. This creates long periods of relative stasis in diastole and increasing particle and cellular residence time at the wall. The dysfunctional wall beneath the stagnant boundary layer begins to accumulate circulating atherogenic cholesteryl fatty acyl esters and triglycerides particles, particularly apolipoprotein B-containing lipoproteins. Oxidative modification of the lipoproteins activates the overlying endothelium to secrete chemokines which attract blood-borne monocytes rolling along the endothelium to tether to the vascular surface made sticky by exposure of adhesion molecules and tissue factor. Diapedesis of firmly attached monocytes traps the cells within the thickened subendothelial space. Thus initiated, the ongoing pathological process generates fatty, occlusive lesions via cholesterol-loaded foam cells, continued recruitment and infiltration of inflammatory and hematopoietic cells, and a progressive accumulation of lipid matrix and smooth muscle proliferation that slowly begins to raise the endothelium and encroach upon the arterial lumen. When grown large enough to reduce the flow of blood and oxygen to vital organs, atherosclerotic plaques produce the chronic clinical syndromes of chest pain (angina pectoris), mini-stroke (transient ischemic attack) and poor circulation (claudication). More complex plaques with ossified cores and degenerating fibrous caps can abruptly rupture leading to acute occlusion of the arteries in which they reside. These generate the critical, life-threatening clinical events of heart attack (myocardial infarction), stroke (cerebrovascular accident) and gangrene (critical limb ischemia).

The treatment-of-choice for end-stage lesions is percutaneous recanalization and implantation of intravascular stents containing antiproliferative compounds that promote healing and enhance patency. Drug-eluting stents are creating by dipping or spraying the stent with a solution that creates a drug layer atop the intact device.

To address the myriad problems associated with permanent metal implants, stents that slowly dissolve after deployment have long been imagined. So-called "bioresorbable vascular scaffolds" (BVS) potentially offer several key biologic and physiologic advantages including, (1) effective scaffolding without the permanence of a metal implant, (2) attenuation of inflammation and chronic foreign body reaction leading to reduced restenosis and enhanced long-term patency, (3) assistance of adaptive vascular remodeling, (4) restoration of physiologic vasoactive function, and (5) facilitation of imaging and surveillance during follow-up. However, bioresorbable vascular scaffolds may cause potential inflammatory response induced by degradation products of the scaffold even after the drug eluting coating has fully absorbed.

Therefore, it would be advantageous to have a stent for use in vasculature that provides longer term release of the drug. At least some of these objectives will be met by the embodiments described below.

SUMMARY

The embodiments herein describe a device for placement within a blood vessel to maintain or enhance blood flow through the blood vessel. The device may comprise one or more balloon-expandable, bioresorbable, vascular stent elements configured to be implanted in the blood vessel as a stent. The stent elements may comprise a scaffold comprising a bioresorbable structural polymer, a coating layer comprising a bioresorbable coating polymer, wherein the coating layer coats the scaffold, and a therapeutic drug, wherein the therapeutic drug is contained within both the coating layer and the scaffold. In an embodiment, the coating layer comprises approximately 80 to 90 percent of the therapeutic drug and the scaffold comprises approximately 10 to 20 percent of the drug. The scaffold may be configured to release the drug as it degrades after the coating layer has completely degraded. The therapeutic drug may prevent or attenuate inflammation, cell dysfunction, cell activation, cell proliferation, neointimal formation, thickening, late atherosclerotic change or thrombosis. In various embodiments the drug is sirolimus, everolimus, zotarolimus, tacrolimus, novolimus, ridafrolimus, temsirolimus, or pimecrolimus.

In some embodiments, the stent may be formed from a material comprising L-lactide, poly(L-lactic acid) (PLLA), poly(D-lactic acid) (PDLA), poly(D,L-lactic acid) (PDLLA), semicrystalline polylactide, polyglycolic acid (PGA), poly(lactic-co-glycolic acid) (PLGA), poly(iodinated desamino tyrosyl-tyrosine ethyl ester) carbonate, ε-caprolactone, polycaprolactone (PCL), salicylate based polymer, polydioxanone (PDS), poly(hydroxybutyrate), poly(hydroxybutyrate-co-valerate), polyorthoester, polyanhydride, poly(glycolic acid-co-trimethylene carbonate), poly(iodinated desaminotyrosyl-tyrosine ethyl ester) carbonate, polyphosphoester, polyphosphoester urethane, poly (amino acids), cyanoacrylates, poly(trimethylene carbonate), poly(iminocarbonate), polyalkylene oxalates, polyphosphazenes, polyiminocarbonates, and aliphatic polycarbonates, fibrin, fibrinogen, cellulose, starch, collagen, polyurethane including polycarbonate urethanes, polyethylene, polyethylene terephthalate, ethylene vinyl acetate, ethylene vinyl alcohol, silicone including polysiloxanes and substituted polysiloxanes, polyethylene oxide, polybutylene terephthalate-co-PEG, PCL-co-PEG, PLA-co-PEG, PLLA-co-PCL, polyacrylates, polyvinyl pyrrolidone, polyacrylamide, or combinations thereof. In an embodiment, the structural polymer comprises a copolymer of L-lactide and ε-caprolactone. In an embodiment, the coating further comprises a non-volatile anti-oxidant.

In another aspect, a method of making a bioresorbable, vascular stent, comprises forming a balloon-expandable, vascular scaffold from a bioresorbable structural polymer using an additive manufacturing process; applying a coating over a surface of the scaffold, wherein the coating comprises a therapeutic drug, a bioresorbable coating polymer configured to provide a matrix for the therapeutic drug on the surface of the scaffold thereby enabling controlled release of the therapeutic drug over time, and a solvent configured to dissolve the therapeutic drug and penetrate the structural polymer thereby inserting the drug within the structural polymer; and drying the coating to remove the solvent thereby trapping the therapeutic drug within the structural polymer. The solvent may be configured to swell or soften the structural polymer of the scaffold. In an embodiment, the structural polymer comprises a copolymer of L-lactide and ε-caprolactone. The solvent may comprise acetonitrile. The coating may further comprise a non-volatile anti-oxidant.

This and other aspects of the present disclosure are described herein.

BRIEF DESCRIPTION OF THE DRAWINGS

Present embodiments have other advantages and features which will be more readily apparent from the following detailed description and the appended claims, when taken in conjunction with the accompanying drawings, in which:

FIG. 5A is a two-dimensional depiction of an element. FIG. 5B shows a magnified view of the cells in FIG. 5A. FIGS. 5C and 5D show the stent element of FIG. 5A in cylindrical form.

DETAILED DESCRIPTION

Figure 1:
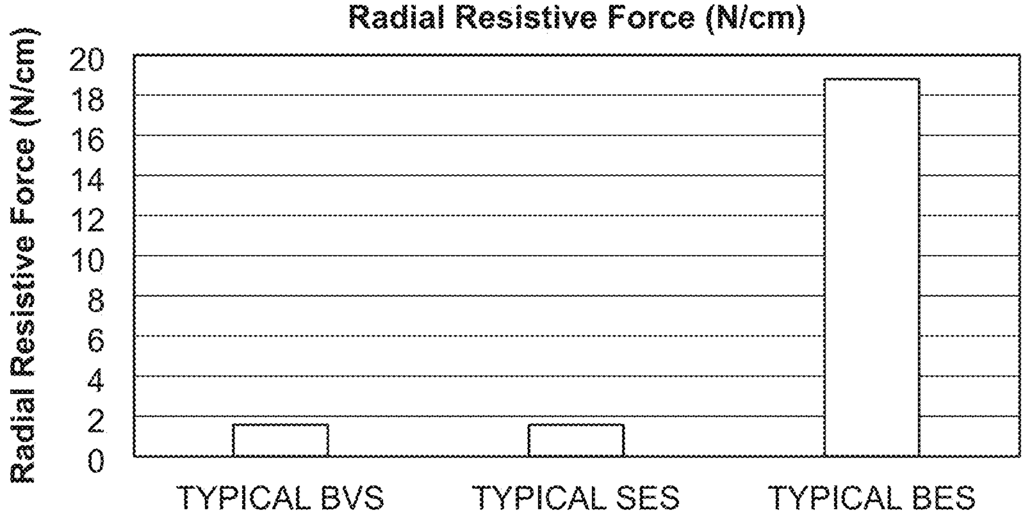
FIG. 1 shows the typical radial resistive forces of intravascular stents.

While the invention has been disclosed with reference to certain embodiments, it will be understood by those skilled in the art that various changes may be made and equivalents may be substituted without departing from the scope of the invention. In addition, many modifications may be made to adapt to a particular situation or material to the teachings of the invention without departing from its scope.

Throughout the specification and claims, the following terms take the meanings explicitly associated herein unless the context clearly dictates otherwise. The meaning of "a", "an", and "the" include plural references. The meaning of "in" includes "in" and "on." Referring to the drawings, like numbers indicate like parts throughout the views. Additionally, a reference to the singular includes a reference to the plural unless otherwise stated or inconsistent with the disclosure herein.

The word "exemplary" is used herein to mean "serving as an example, instance, or illustration." Any implementation described herein as "exemplary" is not necessarily to be construed as advantageous over other implementations.

Various embodiments are described herein with reference to the figures. The figures are not drawn to scale and are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated.

FIG. 1 shows the typical radial resistive forces of intravascular stents. A typical "bioresorbable vascular scaffold" (BVS) or absorbable stent has a radial resistive force of under 2 N/cm. Similarly, a typical self-expanding metal stent (SES) has a radial resistive force of under 2 N/cm. Typical balloon-expandable metal stents (BES) have a much higher radial resistive force, sometimes above 18 N/cm.

The embodiments herein describe the design of a new, intravascular absorbable device that maintains the flow channel (patency) of long blood vessels by providing temporary, rigid, radial support that is far greater than that provided by a typical absorbable or metal self-expanding stent (SES) and commensurate with that provided by a metal balloon-expandable stent (BES). Once implanted, the absorbable device imparts a high degree of radial force to prop open the diseased artery; the force is roughly equivalent to a large diameter, peripheral, balloon-expandable metal stent.

In contrast to most stent patterns which are designed to marry both radial force and longitudinal flexibility, the patterns described herein are specifically tailored to maximize radial force and rigidity and forego longitudinal and axial flexibility.

The devices described herein are multi-element, vascular stents (or "vascular scaffolds"). These stents are comprised of multiple, short, rigid, cylindrical stent segments, or elements, which are separate from one another but may be referred to together as a multi-element stent.

Generally, at least two of the elements of the multi-element stent described herein will be sufficiently rigid to provide a desired level of strength to withstand the stresses of the vessel in which they are placed, such as a tortuous peripheral vessel. At the same time, a multi element stent will also be flexible, due to the fact that it is made up of multiple separate elements, thus allowing for placement within a curved, torturous blood vessel. In some embodiments, at least two of the elements vary in rigidity or radial strength in a multi-element stent. In one embodiment, the outer elements may have a lesser radial strength than the inner elements in a multi-element stent. In another embodiment, a multi-element stent comprises elements having an increasing radial strength serially along the length of the multi-element stent, such as in an AV fistula. Thus, the radial strength of elements may vary and be tailored by known characteristics of a target artery.

Additionally, the multi element stents described herein will usually be balloon-expandable rather than self-expanding, since balloon-expandable stents are typically stronger than self-expanding stents. Each balloon expandable element of the stent may have relatively high radial force (rigidity) due to the described structures and materials. A stent element is defined as being radially rigid if it has a radial strength significantly higher than self-expanding stents that is similar or greater in magnitude to that of traditional, metal balloon-expandable stents, such as those made of steel or cobalt-chromium.

When mounted serially on an inflatable balloon, they can be simultaneously implanted side-by-side in long blood vessels. During motion of the organism, the elements can move independently, maintaining their individual shape and strength while the intervening, non-stented elements of the vessel can twist, bend and rotate unencumbered. The result is a treated vessel with a rigidly maintained flow channel that still enjoys unrestricted flexibility during organismal movement.

The described embodiments exploit the principles that, (1) a rigid device that is deployed via balloon-expansion represents the optimal design of an intravascular stent given its transient effect on the arterial wall and relative ease of precise implantation, (2) a long, rigid device cannot be safely implanted in an artery that bends and twists with skeletal motion, (3) long arteries that bend and twist could be effectively treated with multiple, short BES that allow the intervening, non-stented arterial elements to move unencumbered, (4) the length, number and spacing of the stent elements could be determined by the known and predictable bending characteristics of the target arteries, and (5) arteries need only be scaffolded transiently; late dissolution of the stent will have little effect on the long-term effectiveness of treatment.

Figures 2A, 2B:
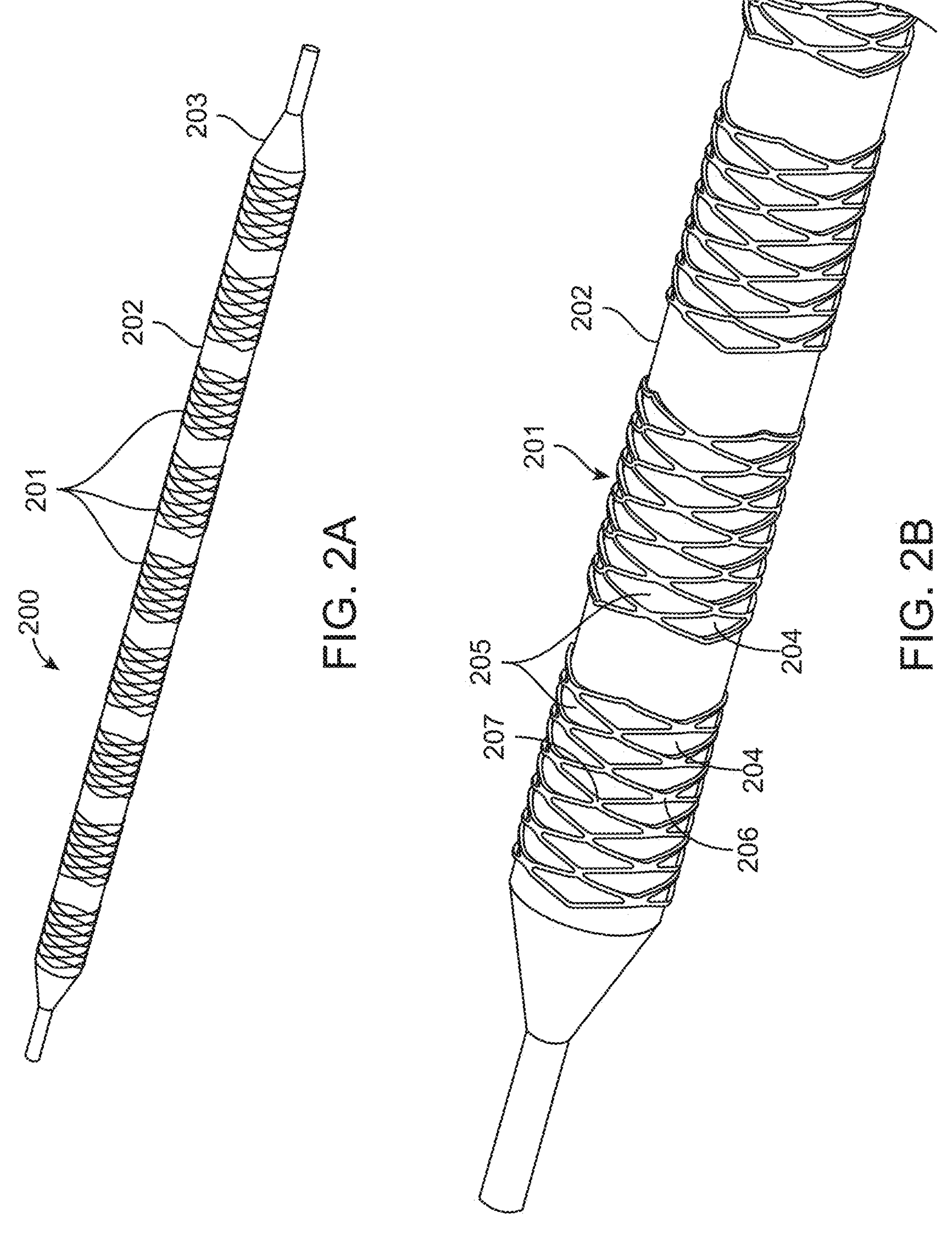
FIG. 2A illustrates one embodiment of a multi-element stent.
FIG. 2B is a magnified view of the stent elements in FIG. 2A.

One embodiment of the fully assembled device in shown in FIG. 2A. A single balloon inflation and device deployment can treat a long segment of diseased artery while still preserving the critical ability of the artery to bend with skeletal motion such as sitting or walking. Multi-element stent 200 comprises multiple stent elements 201. Individual balloon-expandable stent elements 201 are crimped onto an inflatable balloon 203 to facilitate delivery. FIG. 2B is a magnified view of the stent elements 201 in FIG. 2A. Individual elements 201 are positioned serially along a longitudinal length of the balloon 203 and spaced such that the stent elements 201 do not touch one another. Further, the spacing is such that after deployment, the stent elements 201 do not touch or overlap during skeletal movement. The number of elements 201, length of elements, and gap 202 between elements 201 may vary depending on the target vessel location. In an embodiment, each element 201 in the multi-element stent 200 has the same length. In multi-element stents having three or more elements 201, and thus two or more gaps 202, the gaps may be of the same length.

Figure 3A:
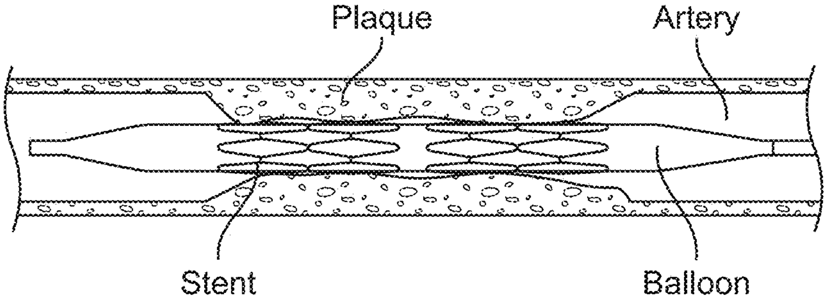
FIGS. 3A-3C depict deployment of a balloon-expandable multi-element stent.
Figure 3B:
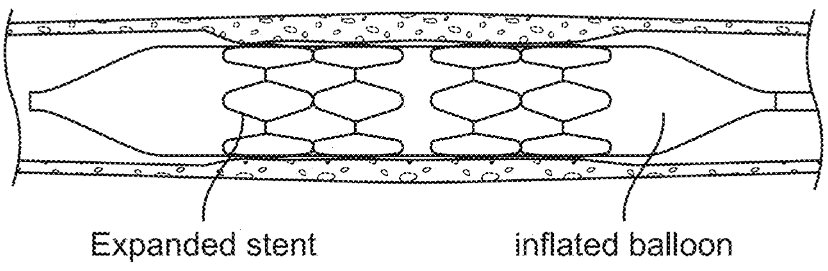
Figure 3C:
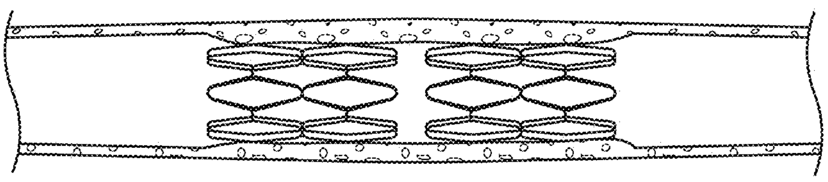

FIGS. 3A-3C depict deployment of a balloon-expandable multi-element stent. In FIG. 3A a multi-element stent mounted on a balloon is advanced to the lesion. In FIG. 3B the balloon and stent are expanded. In FIG. 3C the balloon is withdrawn leaving the multi-element stent still within the artery.

Figure 4A:
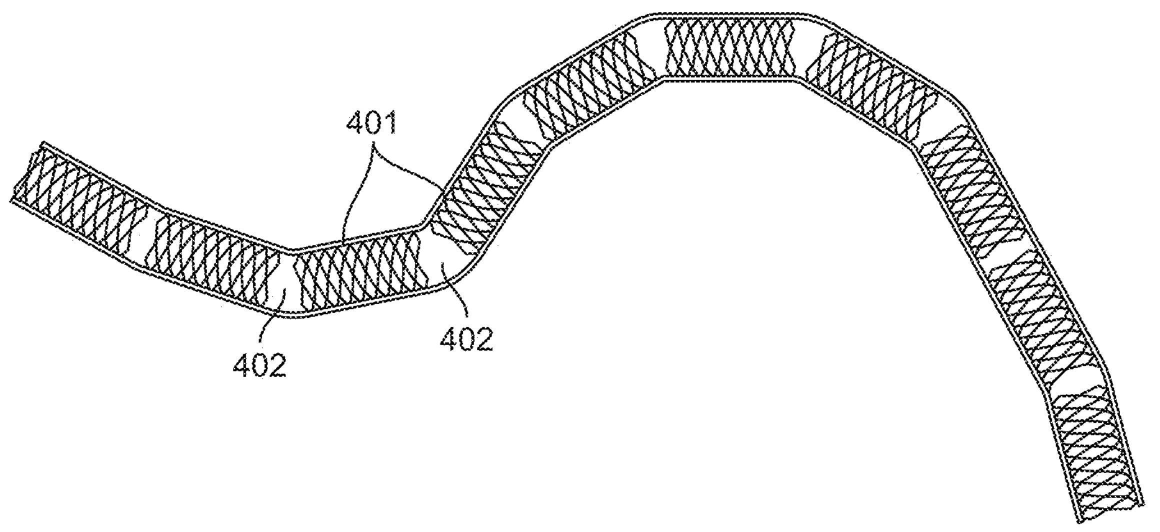
FIG. 4A shows an implanted multi-element stent in a popliteal artery during full flexion of the hip and knee.
Figure 4B:
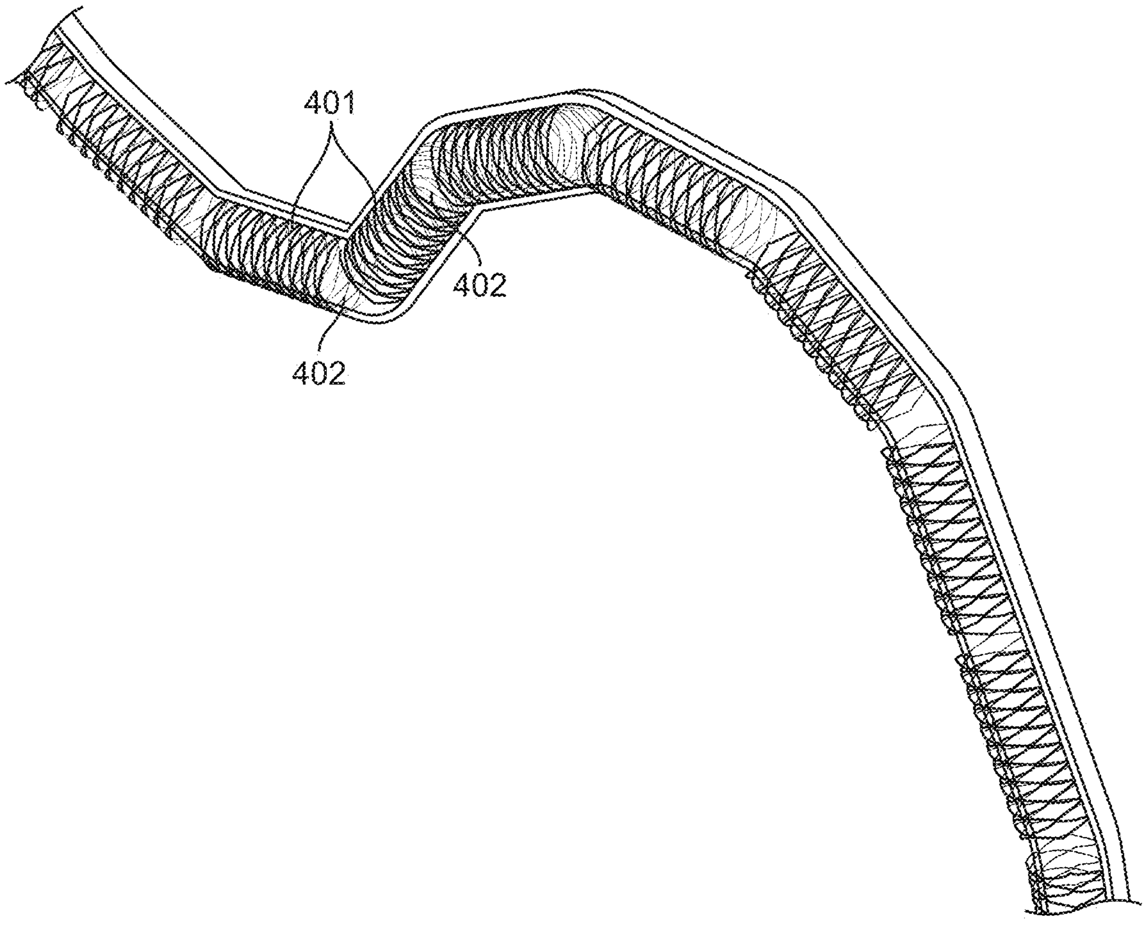
FIG. 4B depicts the implanted device of FIG. 4A shown in three dimensions.
Figures 5A, 5B, 5C:
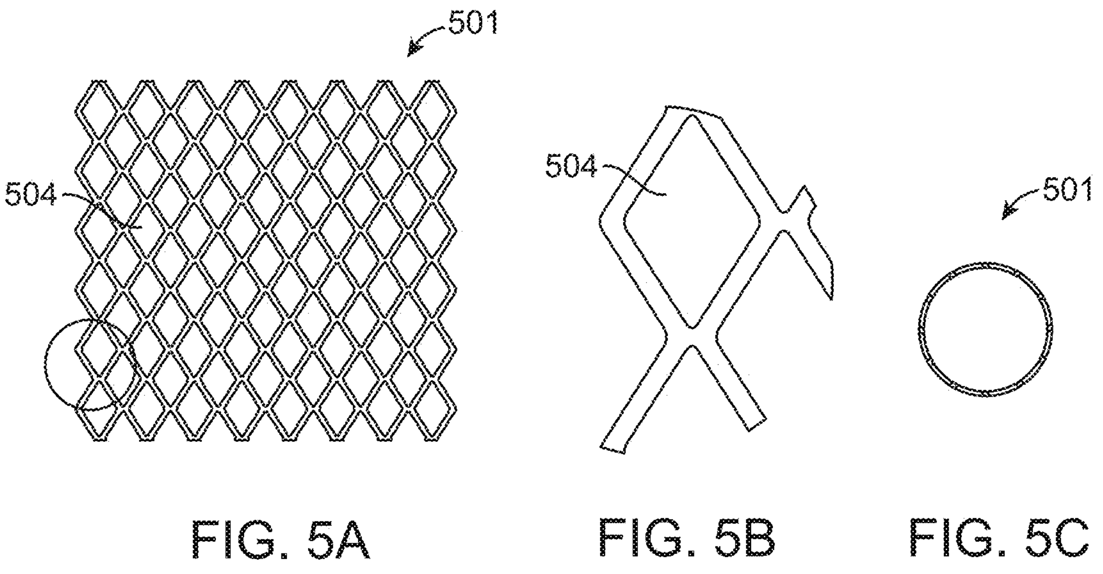
FIGS. 5A-5D show an embodiment of a stent pattern.
Figure 5D:
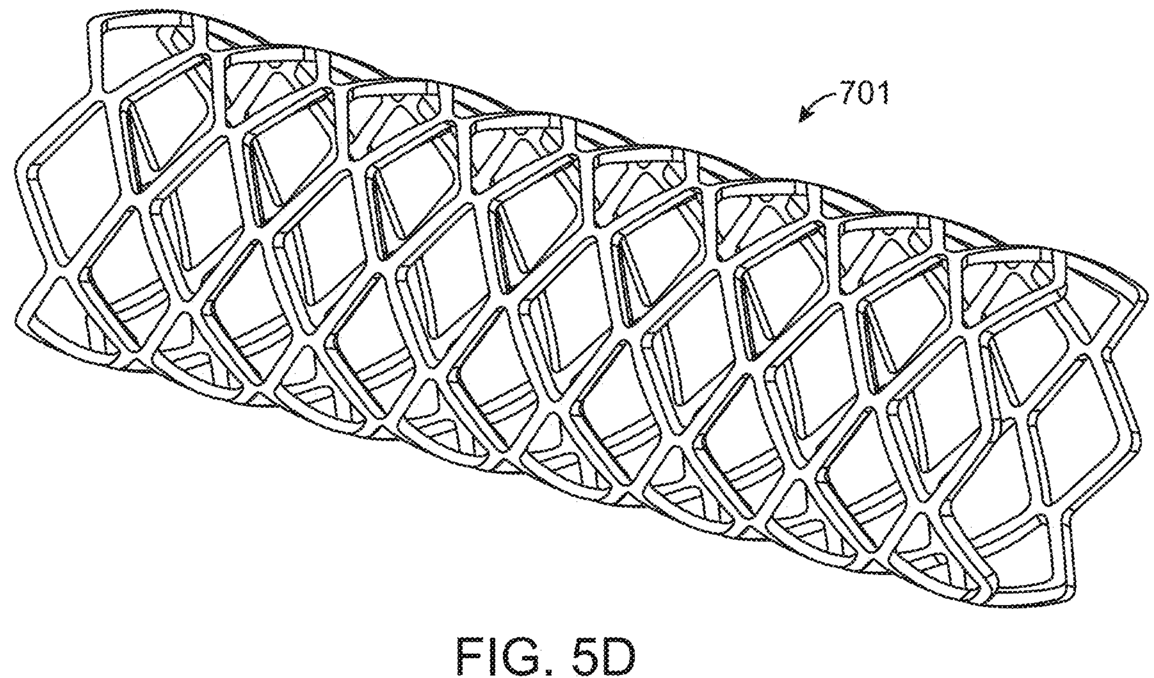

FIG. 4A shows an implanted multi-element stent in a popliteal artery during full flexion of the hip and knee. FIG. 4B depicts the implanted device of FIG. 4A shown in three dimensions. The individual stent elements 401 are spaced such that they do not overlap even when the artery is highly bent. Unencumbered arterial movement is afforded through flexion or extension of the unstented gaps 402.

Stent elements may comprise various shapes and configurations. Some or all of the stent elements may comprise closed-cell structures formed by intersecting struts. Closed-cell structures may comprise diamond, square, rectangular, parallelogrammatic, triangular, pentagonal, hexagonal, heptagonal, octagonal, clover, lobular, circular, elliptical, and/or ovoid geometries. Closed-cells may also comprise slotted shapes such as H-shaped slots, I-shaped slots, J-shaped slots, and the like. Additionally or alternatively, stent may comprise open cell structures such as spiral structures, serpentine structures, zigzags structures, etc. Strut intersections may form pointed, perpendicular, rounded, bullnosed, flat, beveled, and/or chamfered cell corners. In an embodiment, stent may comprise multiple different cells having different cell shapes, orientations, and/or sizes. Various cell structures have been described in PCT International Application Number PCT/US16/20743, entitled "MULTI-ELEMENT BIORESORBABLE INTRAVASCULAR STENT", PCT International Application Number PCT/US20/19132, entitled "ABSORBABLE INTRAVASCULAR DEVICES THAT EXHIBIT THEIR GREATEST RADIAL STRENGTH AT THEIR NOMINAL DIAMETERS", and PCT International Application Number PCT/US19/35861, entitled "ABSORBABLE INTRAVASCULAR DEVICES THAT SHORTEN UPON EXPANSION CREATING SPACE FOR VASCULAR MOVEMENT", the full disclosures of which are herein incorporated by reference.

Returning to FIG. 2B, in this exemplary embodiment, the stent elements 201 have a diamond shaped closed-cell pattern. Elements 201 comprise intermixed diamond shaped closed cells 204, 205. Diamond shaped cells 204 may be aligned in the longitudinal and/or the circumferential directions in a repeating pattern. Similarly, diamond shaped cells 205 may be aligned in the longitudinal and/or the circumferential directions in a repeating pattern. Additionally or alternatively, diamond shaped cells 204 and diamond shaped cells 205 may be helically aligned in an alternating pattern. In an embodiment, diamond shaped cells 204 and diamond shaped cells 205 are circumferentially offset. Additionally, diamond shaped cells 205 may be formed at a central location between four adjacent diamond shaped cells 204. The width of struts 206 between two corners of longitudinally aligned diamond shaped cells 204 are larger than the width of struts 207 between two corners of longitudinally aligned diamond shaped cells 205.

Figure 6:
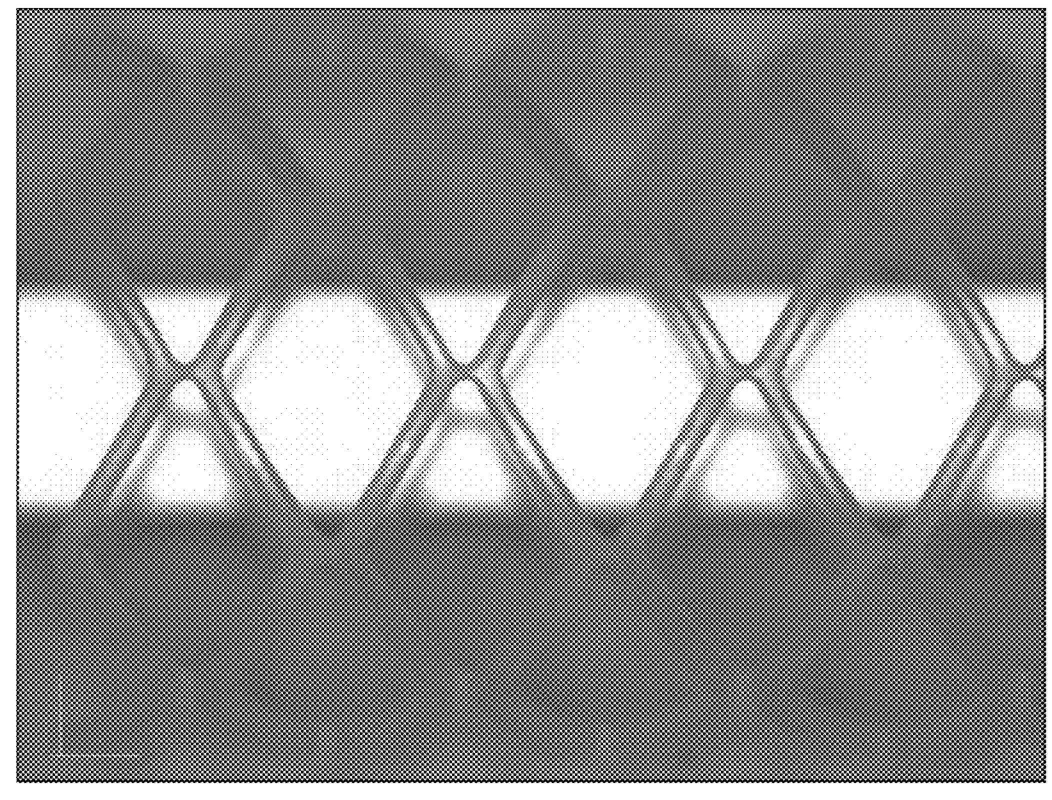
FIG. 6 shows a laser cut stent.

One embodiment of a stent pattern is shown in shown in FIGS. 5A-5D. The stent elements 501 have a diamond shaped closed-cell pattern with relatively thick strut widths and obliquely-angled links. Elements 501 comprise diamond shaped closed cells 504. Elements 501 may comprise wide struts 506 of 225 microns or larger. Elements 501 may similarly comprise thick struts 506 of 225 microns or larger. In an embodiment, elements 501 comprise struts 506 with a width and/or thickness of approximately 250 microns. The width and/or the height of struts 506 between two corners of diamond shaped cells 504 may be larger or smaller than the width and/or height of struts 506 forming the sides of diamond shaped cells 504. An example of an actual laser-cut stent designed herein is shown in FIG. 6.

Described herein are various designs of resorbable, drug-containing stents having a drug integrated within the scaffold structural material. The scaffold may be comprised of structural biodegradable polymer or co-polymer in a slotted tube design, over which is applied a drug containing coating. The coating may be comprised of a therapeutic drug and solvent(s), such that the solvent dissolves the drug, and swells and/or softens the structural polymer but does not appreciably dissolve or deform it in the application process. The coating optionally contains an organic matrix (biodegradable polymer, oligomer or other excipient) and/or anti-oxidants which are soluble in the coating solvent or solvents. When applied by spray, dip, or trough coating methods, the drug-solvent coating penetrates the base polymer and inserts drug within it, in addition to applying drug to the scaffold surface. Drying, either at room temperature or elevated temperature and optionally in vacuum, removes the solvent and traps the absorbed drug within the scaffold structural polymer. In an embodiment, the coating contains a dissolved biodegradable polymer that is compatible with the structural polymer and anti-oxidants to preserve drug stability. The presence of a polymer in the coating provides a matrix for the drug on the scaffold surface, enabling controlled release over time via diffusion.

The stents described herein may be formed from various different materials. In an embodiment, stents may be formed a polymer or co-polymer. In various alternative embodiments, the stent or stent element may be made from any suitable bioresorbable material such that it will dissolve non-toxically in the human body, such as but not limited to polyesters such as Polylactic acid, Poly(ε-caprolactone), Polyglycolic acid, and Polyhydroxyalkanoate, amino acid based polymers such as Polyesteramide, polycarbonates such as Polytrimethylene carbonate as well as any and all copolymers of the types described herein. In an embodiment, the stent polymer is comprised of a 95/5 molar ratio of L-lactide and ε-caprolactone, Purasorb 9538. In other embodiments, other molar ratios may be used such as approximately 80/20-90/10, approximately 90/10-95/5, or approximately 95/5-98/2.

In various embodiments, any suitable polymer or copolymer may be used to construct the stent. The term "polymer" is intended to include a product of a polymerization reaction inclusive of homopolymers, copolymers, terpolymers, etc., whether natural or synthetic, including random, alternating, block, graft, branched, cross-linked, blends, compositions of blends and variations thereof. The polymer may be in true solution, saturated, or suspended as particles or supersaturated in the beneficial agent. The polymer can be biocompatible, or biodegradable. For purpose of illustration and not limitation, the polymeric material may include, but is not limited to, L-lactide, poly(D-lactic acid) (PDLA), poly(D,L-lactic acid) (PDLLA), poly(iodinated desamino tyrosyl-tyrosine ethyl ester) carbonate, poly(lactic-co-glycolic acid) (PLGA), poly(iodinated desaminotyrosyl-tyrosine ethyl ester) carbonate, salicylate based polymer, semicrystalline polylactide, phosphorylcholine, ε-caprolactone, polycaprolactone (PCL), poly-D,L-lactic acid, poly-L-lactic acid, poly(lactideco-glycolide), poly(hydroxybutyrate), poly(hydroxybutyrate-co-valerate), polydioxanone (PDS), polyorthoester, polyanhydride, poly(glycolic acid), poly(glycolic acid-co-trimethylene carbonate), polyphosphoester, polyphosphoester urethane, poly(amino acids), cyanoacrylates, poly(trimethylene carbonate), poly(iminocarbonate), polyalkylene oxalates, polyphosphazenes, polyiminocarbonates, and aliphatic polycarbonates, fibrin, fibrinogen, cellulose, starch, collagen, polyurethane including polycarbonate urethanes, polyethylene, polyethylene terephthalate, ethylene vinyl acetate, ethylene vinyl alcohol, silicone including polysiloxanes and substituted polysiloxanes, polyethylene oxide, polybutylene terephthalate-co-PEG, PCL-co-PEG, PLA-co-PEG, PLLA-co-PCL, polyacrylates, polyvinyl pyrrolidone, polyacrylamide, and combinations thereof. Non-limiting examples of other suitable polymers include thermoplastic elastomers in general, polyolefin elastomers, EPDM rubbers and polyamide elastomers, and biostable plastic material including acrylic polymers, and its derivatives, nylon, polyesters and expoxies.

In some embodiments, the stent may include one or more coatings, with materials like poly-L-lactide (PLLA) or poly (D,L-lactic acid) (PDLLA). These materials are merely examples, however, and should not be seen as limiting the scope of the invention. The coating may comprise a drug and a solvent capable of dissolving the drug and swelling or softening the scaffold structural polymer. The solvent may be any single solvent or a combination of solvents. For purpose of illustration and not limitation, examples of suitable solvents include water, aliphatic hydrocarbons, aromatic hydrocarbons, alcohols, ketones, dimethyl sulfoxide, tetrahydrofuran, dihydrofuran, dimethylacetamide, acetonitrile, acetates, and combinations thereof. In an embodiment wherein the stent polymer is comprised of a 95/5 molar ratio of L-lactide and ε-caprolactone, one suitable solvent is acetonitrile.

The therapeutic drug may be any agent intended to prevent or attenuate pathologic consequences of intraluminal intervention such as inflammation, cell dysfunction, cell activation, cell proliferation, neointimal formation, thickening, late atherosclerotic change and/or thrombosis. In an embodiment, the drug may be Sirolimus and/or its derivatives. Examples of such therapeutic agents include, but are not limited to, antithrombotics, anticoagulants, antiplatelet agents, anti-lipid agents, thrombolytics, antiproliferatives, anti-inflammatories, agents that inhibit hyperplasia, smooth muscle cell inhibitors, antibiotics, growth factor inhibitors, cell adhesion inhibitors, cell adhesion promoters, antimitotics, antifibrins, antioxidants, anti-neoplastics, agents that promote endothelial cell recovery, matrix metalloproteinase inhibitors, anti-metabolites, antiallergic substances, viral vectors, nucleic acids, monoclonal antibodies, inhibitors of tyrosine kinase, antisense compounds, oligonucleotides, cell permeation enhancers, hypoglycemic agents, hypolipidemic agents, proteins, nucleic acids, agents useful for erythropoiesis stimulation, angiogenesis agents, anti-ulcer/anti-reflux agents, and anti-nauseants/anti-emetics, PPAR alpha agonists such as fenofibrate, PPAR-gamma agonists selected such as rosiglitazaone and pioglitazone, sodium heparin, LMW heparins, heparoids, hirudin, argatroban, forskolin, vapriprost, prostacyclin and prostacylin analogues, dextran, D-phe-pro-arg-chloromethylketone (synthetic anti-thrombin), glycoprotein IIb/IIIa (platelet membrane receptor antagonist antibody), recombinant hirudin, thrombin inhibitors, indomethacin, phenyl salicylate, beta-estradiol, vinblastine, ABT-627 (astrasentan), testosterone, progesterone, paclitaxel, methotrexate, fotemusine, RPR-101511A, cyclosporine A, vincristine, carvediol, vindesine, dipyridamole, methotrexate, folic acid, thrombospondin mimetics, estradiol, dexamethasone, metrizamide, iopamidol, iohexol, iopromide, iobitridol, iomeprol, iopentol, ioversol, ioxilan, iodixanol, and iotrolan, antisense compounds, inhibitors of smooth muscle cell proliferation, lipid-lowering agents, radiopaque agents, antineoplastics, HMG CoA reductase inhibitors such as lovastatin, atorvastatin, simvastatin, pravastatin, cerivastatin and fluvastatin, and combinations thereof.

Examples of antithrombotics, anticoagulants, antiplatelet agents, and thrombolytics include, but are not limited to, sodium heparin, unfractionated heparin, low molecular weight heparins, such as dalteparin, enoxaparin, nadroparin, reviparin, ardoparin and certaparin, heparinoids, hirudin, argatroban, forskolin, vapriprost, prostacyclin and prostacylin analogues, dextran, D-phe-pro-arg-chloromethylketone (synthetic antithrombin), dipyridamole, glycoprotein IIb/IIIa (platelet membrane receptor antagonist antibody), recombinant hirudin, and thrombin inhibitors such as bivalirudin, thrombin inhibitors, and thrombolytic agents, such as urokinase, recombinant urokinase, pro-urokinase, tissue plasminogen activator, ateplase and tenecteplase.

Examples of cytostatic or antiproliferative agents include, but are not limited to, rapamycin and its analogs, including everolimus, zotarolimus, tacrolimus, novolimus, ridafrolimus, temsirolimus, and pimecrolimus, angiopeptin, angiotensin converting enzyme inhibitors, such as captopril, cilazapril or lisinopril, calcium channel blockers, such as nifedipine, amlodipine, cilnidipine, lercanidipine, benidipine, trifluperazine, diltiazem and verapamil, fibroblast growth factor antagonists, fish oil (omega 3-fatty acid), histamine antagonists, lovastatin, topoisomerase inhibitors, such as etoposide and topotecan, as well as antiestrogens such as tamoxifen.

Examples of anti-inflammatory agents include, but are not limited to, colchicine and glucocorticoids, such as betamethasone, cortisone, dexamethasone, budesonide, prednisolone, methylprednisolone and hydrocortisone. Non-steroidal anti-inflammatory agents include, but are not limited to, flurbiprofen, ibuprofen, ketoprofen, fenoprofen, naproxen, diclofenac, diflunisal, acetominophen, indomethacin, sulindac, etodolac, diclofenac, ketorolac, meclofenamic acid, piroxicam and phenylbutazone.

Examples of antineoplastic agents include, but are not limited to, alkylating agents including altretamine, bendamucine, carboplatin, carmustine, cisplatin, cyclophosphamide, fotemustine, ifosfamide, lomustine, nimustine, prednimustine, and treosulfin, antimitotics, including vincristine, vinblastine, paclitaxel, docetaxel, antimetabolites including methotrexate, mercaptopurine, pentostatin, trimetrexate, gemcitabine, azathioprine, and fluorouracil, antibiotics, such as doxorubicin hydrochloride and mitomycin, and agents that promote endothelial cell recovery such as estradiol.

Antiallergic agents include, but are not limited to, permirolast potassium nitroprusside, phosphodiesterase inhibitors, prostaglandin inhibitors, suramin, serotonin blockers, steroids, thioprotease inhibitors, triazolopyrimidine, and nitric oxide.

The coating may comprise a polymer that is soluble in the chosen coating solvent and chemically compatible with the base structural polymer, so as to provide adequate interfacial adhesion. The polymer also provides a solid matrix to house the mostly amorphous drug, providing controlled release into the arterial tissue via diffusion. For the example of a 95/5 ratio of L-lactide and ε-caprolactone as the structural polymer, acetonitrile as the coating solvent, and Sirolimus as the drug, the coating polymer may be a polymer of poly-L-lactide (PLLA). For Sirolimus or its derivatives, inclusion of a non-volatile anti-oxidant in the formulation is useful to retard drug degradation.

An embodiment of the coating formulation comprises Sirolimus, acetonitrile, PLLA and an anti-oxidant. The ratio of PLLA to Sirolimus is 70/30. When applied over a 95/5 ratio of L-lactide and ε-caprolactone scaffold and dried, about 10 to 20 percent of the Sirolimus is deposited into the scaffold, while the remainder, 80 to 90 percent, resides in the surface coating matrix.

In an embodiment, the molecular weight of the coating polymer is lower than the molecular weight of the structural polymer, and degrades faster and loses mass sooner than the structural polymer. Therefore the coating matrix, and all of the drug contained within the surface coating layer, will be gone when the structural polymer is still present in the tissue. As the scaffold polymer degrades it liberates acidic monomers such as lactic acid and 6-hydroxyhexanoic acid, which can induce tissue inflammation. Having a drug with anti-inflammatory character embedded within the scaffold polymer counters inflammation and enhances the healing response by providing late stage anti-inflammatory effect.

Figure 7:
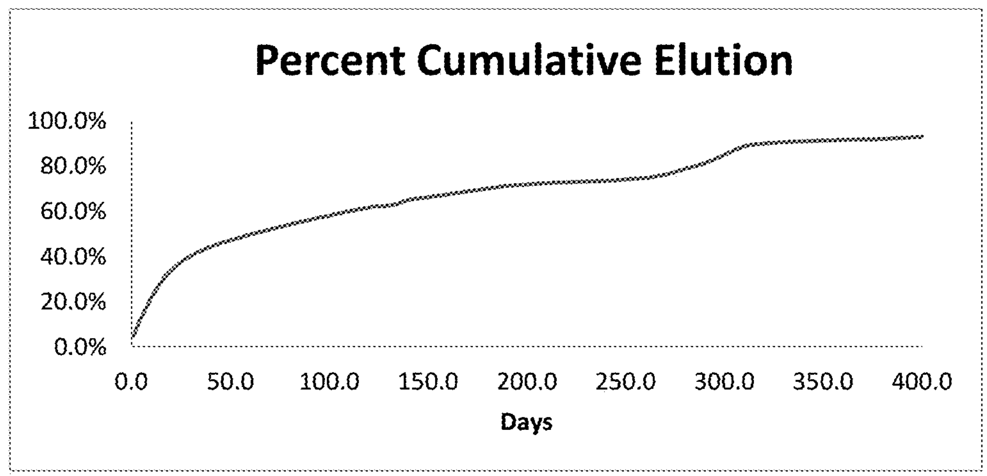
FIG. 7 shows the drug release of a stent over time

Stents described herein may show a three or four phase drug release. In an embodiment the stent provides an initial high release rate of the drug from the coating for a short period after implantation. Thereafter, the release a more gradual release of the drug from the coating. After the coating has degraded completely, the scaffold will continue to release the drug at a lower rate until all of the drug has eluted. FIG. 7 shows the drug release of a stent over time. The graph illustrates the cumulative percent release of Sirolimus from the coated scaffold. A high sustained level of release is shown from approximately days 1 to 23. This is followed by a more gradual release until approximately day 270. The process of coating mass degradation at this time period will cause the release of the remaining drug in the coating from approximately days 270 to 310. Drug that remains in the scaffold itself will continue to elute beyond this point at a low rate until the scaffold mass degrades.

Stents may be manufactured using an additive or a subtractive method. In any of the described embodiments, stents or stent elements may be manufactured as a sheet and wrapped into cylindrical form. Alternatively, stents or stent elements may be manufactured in cylindrical form using an additive manufacturing process. In an embodiment, stents maybe formed by extruding a material into a cylindrical tubing. In some embodiments, a longer stent element, may be formed during the manufacturing process and then cut into smaller stent elements/elements to provide a multi-element stent. In an embodiment, stent tubing may be laser cut with a pattern to form a stent element.

Figure 8:
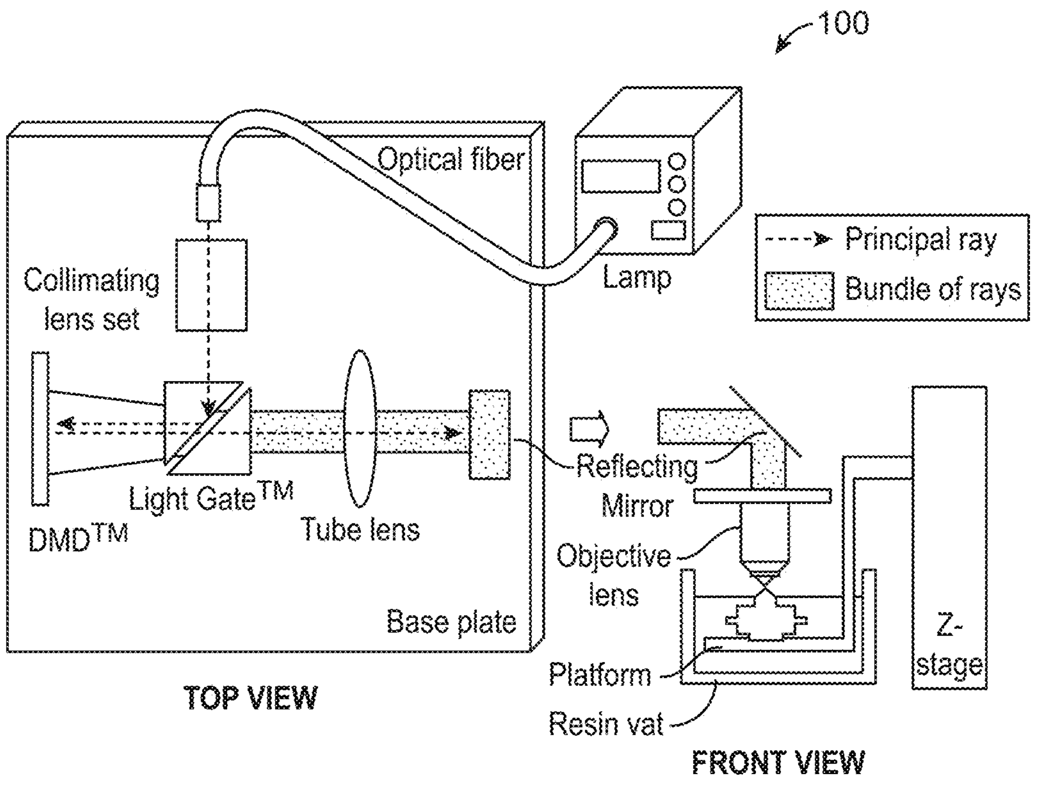
FIG. 8 is a schematic diagram of a micro-stereolithograph used to create a stent, according to one embodiment.

Referring now to FIG. 8, in one embodiment, stents may be manufactured using a micro-stereolithography system 100 (or "3D printing system"). Several examples of currently available systems that might be used in various embodiments include, but are not limited to: MakiBox A6, Makible Limited, Hong Kong; CubeX, 3D Systems, Inc., Circle Rock Hill, SC; and 3D-Bioplotter, (EnvisionTEC GmbH, Gladbeck, Germany).

The micro-stereolithography system may include an illuminator, a dynamic pattern generator, an image-former and a Z-stage. The illuminator may include a light source, a filter, an electric shutter, a collimating lens and a reflecting mirror that projects a uniformly intense light on a digital mirror device (DMD), which generates a dynamic mask. FIG. 10 shows some of these components of one embodiment of the micro-stereolithography system 100, including a DMD board, Z-stage, lamp, platform, resin vat and an objective lens. The details of 3D printing/micro-stereolithography systems and other additive manufacturing systems will not be described here, since they are well known in the art. However, according to various embodiments, any additive manufacturing system or process, whether currently known or hereafter developed, may potentially be used to fabricate stents within the scope of the present invention. In other words, the scope of the invention is not limited to any particular additive manufacturing system or process.

In one embodiment, the system 100 may be configured to fabricate stents using dynamic mask projection micro-stereolithography. In one embodiment, the fabrication method may include first producing 3D microstructural scaffolds by slicing a 3D model with a computer program and solidifying and stacking images layer by layer in the system. In one embodiment, the reflecting mirror of the system is used to project a uniformly intense light on the DMD, which generates a dynamic mask. The dynamic pattern generator creates an image of the sliced section of the fabrication model by producing a black-and-white region similar to the mask. Finally, to stack the images, a resolution Z-stage moves up and down to refresh the resin surface for the next curing. The Z-stage build subsystem, in one embodiment, has a resolution of about 100 nm and includes a platform for attaching a substrate, a vat for containing the polymer liquid solution, and a hot plate for controlling the temperature of the solution. The Z-stage makes a new solution surface with the desired layer thickness by moving downward deeply, moving upward to the predetermined position, and then waiting for a certain time for the solution to be evenly distributed.

Although particular embodiments have been shown and described, they are not intended to limit the invention. Various changes and modifications may be made to any of the embodiments, without departing from the spirit and scope of the invention. The invention is intended to cover alternatives, modifications, and equivalents.

What is claimed is:

1. A method of making a bioresorbable, vascular stent, the method comprising:

forming a balloon-expandable, vascular scaffold from a bioresorbable structural polymer using an additive manufacturing process;

applying a coating over a surface of the scaffold, wherein the coating comprises a therapeutic drug, a bioresorbable coating polymer configured to provide a matrix for the therapeutic drug on the surface of the scaffold thereby enabling controlled release of the therapeutic drug over time, and a solvent configured to dissolve the therapeutic drug and penetrate the structural polymer thereby inserting the drug within the structural polymer; and drying the coating to remove the solvent thereby trapping the therapeutic drug within the structural polymer.

2. The method of claim 1, wherein the coating comprises approximately 80 to 90 percent of the therapeutic drug and the scaffold comprises approximately 10 to 20 percent of the drug.

3. The method of claim 1, wherein the solvent is configured to swell or soften the structural polymer of the scaffold.

4. The method of claim 1, wherein the scaffold is configured to release the therapeutic drug as it degrades after the coating layer has completely degraded.

5. The method of claim 1, wherein the therapeutic drug prevents or attenuates inflammation, cell dysfunction, cell activation, cell proliferation, neointimal formation, thickening, late atherosclerotic change or thrombosis.

6. The method of claim 5, wherein the drug is sirolimus, everolimus, zotarolimus, tacrolimus, novolimus, ridafrolimus, temsirolimus, or pimecrolimus.

* * * * *